(12) United States Patent
Lareau et al.

(10) Patent No.: US 8,337,451 B2
(45) Date of Patent: Dec. 25, 2012

(54) RECIRCULATION MINIMIZING CATHETER

(75) Inventors: Raymond Lareau, Westford, MA (US); Mark Wolfson, Wellesley, MA (US)

(73) Assignee: Angio Dynamics, Inc., Latham, NY (US)

( * ) Notice: Subject to any disclaimer, the term of this patent is extended or adjusted under 35 U.S.C. 154(b) by 0 days.

(21) Appl. No.: 12/254,532

(22) Filed: Oct. 20, 2008

(65) Prior Publication Data

US 2009/0187141 A1 Jul. 23, 2009

Related U.S. Application Data

(60) Provisional application No. 60/981,343, filed on Oct. 19, 2007, provisional application No. 60/981,371, filed on Oct. 19, 2007.

(51) Int. Cl.
*A61M 3/00* (2006.01)

(52) U.S. Cl. .......................................................... 604/43

(58) Field of Classification Search .............. 604/27–29, 604/284, 39–43
See application file for complete search history.

(56) References Cited

U.S. PATENT DOCUMENTS

| | | |
|---|---|---|
| 3,094,124 A | 6/1963 | Birtwell |
| 3,438,375 A | 4/1969 | Ericson |
| 3,978,157 A | 8/1976 | Bottenbruch et al. |
| 4,054,139 A | 10/1977 | Crossley |
| 4,142,525 A | 3/1979 | Binard et al. |
| 4,403,983 A | 9/1983 | Edelman et al. |
| 4,468,224 A | 8/1984 | Enzmann et al. |
| 4,469,483 A | 9/1984 | Becker et al. |
| 4,483,688 A | 11/1984 | Akiyama |
| 4,563,180 A | 1/1986 | Jervis et al. |
| 4,569,673 A | 2/1986 | Tesi |
| 4,592,920 A | 6/1986 | Murtfeldt |
| 4,603,152 A | 7/1986 | Laurin et al. |
| 4,623,327 A | 11/1986 | Mahurkar |
| 4,769,005 A | 9/1988 | Ginsburg et al. |
| 4,902,503 A | 2/1990 | Umemura et al. |
| 4,944,726 A | 7/1990 | Hilal et al. |
| 5,019,096 A | 5/1991 | Fox et al. |
| 5,059,170 A | 10/1991 | Cameron |

(Continued)

FOREIGN PATENT DOCUMENTS

DE 20208420 10/2002

(Continued)

OTHER PUBLICATIONS

Carbothane MSDS from Microspecorporation.com accessed Thursday Aug. 4, 2011. http://www.microspecorporation.com/materials.php?id=5.

(Continued)

*Primary Examiner* — Kevin C Sirmons
*Assistant Examiner* — Imani Hayman
(74) *Attorney, Agent, or Firm* — Ryan D. Artis

(57) ABSTRACT

A flow control tip for a catheter comprises a partition dividing the catheter into first and second lumens, a first orifice fluidly connected to the first lumen and a second orifice fluidly connected to the second lumen, the first orifice being proximal to the second orifice, an elongate protrusion extending along a portion of the partition substantially along a centerline of the elongated body and a deflecting surface extending at an angle relative to the protrusion to direct flow from the first orifice away from the centerline.

23 Claims, 7 Drawing Sheets

U.S. PATENT DOCUMENTS

| | | | |
|---|---|---|---|
| 5,125,893 | A | 6/1992 | Dryden |
| 5,133,742 | A | 7/1992 | Pinchuk |
| 5,151,231 | A | 9/1992 | Lambert et al. |
| 5,205,834 | A | 4/1993 | Moorehead et al. |
| 5,229,431 | A | 7/1993 | Pinchuk |
| 5,249,598 | A | 10/1993 | Schmidt |
| 5,300,048 | A | 4/1994 | Drewes et al. |
| 5,374,245 | A * | 12/1994 | Mahurkar ............ 604/43 |
| 5,403,291 | A | 4/1995 | Abrahamson |
| 5,405,340 | A | 4/1995 | Fageol et al. |
| 5,472,417 | A | 12/1995 | Martin et al. |
| 5,509,897 | A | 4/1996 | Twardowski et al. |
| 5,542,937 | A | 8/1996 | Chee et al. |
| 5,569,182 | A * | 10/1996 | Twardowski et al. ........ 604/43 |
| 5,575,769 | A | 11/1996 | Vaillancourt |
| 5,614,136 | A | 3/1997 | Pepin et al. |
| 5,662,913 | A | 9/1997 | Capelli |
| 5,683,640 | A | 11/1997 | Miller et al. |
| 5,725,510 | A | 3/1998 | Hartmann et al. |
| 5,800,414 | A | 9/1998 | Cazal |
| 5,843,161 | A | 12/1998 | Solovay |
| 5,879,499 | A | 3/1999 | Corvi |
| 5,928,174 | A | 7/1999 | Gibbins |
| 6,033,393 | A | 3/2000 | Balbirz et al. |
| 6,093,180 | A | 7/2000 | Elsberry |
| 6,177,522 | B1 | 1/2001 | Brady et al. |
| 6,197,846 | B1 | 3/2001 | Cmbe et al. |
| 6,200,338 | B1 | 3/2001 | Solomon et al. |
| 6,217,566 | B1 | 4/2001 | Ju et al. |
| 6,227,200 | B1 | 5/2001 | Crump et al. |
| 6,280,423 | B1 | 8/2001 | Davey et al. |
| 6,315,789 | B1 | 11/2001 | Cragg |
| 6,355,858 | B1 | 3/2002 | Gibbins |
| 6,368,658 | B1 | 4/2002 | Schwarz et al. |
| 6,375,637 | B1 | 4/2002 | Campbell et al. |
| 6,409,700 | B1 | 6/2002 | Siegel, Jr. et al. |
| 6,442,415 | B1 | 8/2002 | Bis et al. |
| 6,446,671 | B2 | 9/2002 | Armenia et al. |
| 6,517,520 | B2 | 2/2003 | Chang et al. |
| 6,530,951 | B1 | 3/2003 | Bates et al. |
| 6,545,097 | B2 | 4/2003 | Pinchuk et al. |
| 6,595,966 | B2 | 7/2003 | Davey et al. |
| 6,605,751 | B1 | 8/2003 | Gibbins et al. |
| 6,777,466 | B2 | 8/2004 | Eckstein et al. |
| 6,819,951 | B2 | 11/2004 | Patel et al. |
| 6,897,349 | B2 | 5/2005 | Gibbins et al. |
| 6,938,668 | B2 | 9/2005 | Whicher et al. |
| 7,179,849 | B2 | 2/2007 | Terry |
| 7,264,858 | B2 | 9/2007 | Belliveau et al. |
| 7,410,602 | B2 | 8/2008 | Davey et al. |
| 2001/0037065 | A1 | 11/2001 | Graf et al. |
| 2002/0082559 | A1 | 6/2002 | Chang et al. |
| 2002/0091362 | A1 | 7/2002 | Maginot et al. |
| 2003/0065355 | A1 | 4/2003 | Weber |
| 2003/0203991 | A1 | 10/2003 | Schottman et al. |
| 2004/0068241 | A1 | 4/2004 | Fischer, Jr. |
| 2004/0068251 | A1 | 4/2004 | Chan et al. |
| 2004/0068315 | A1 | 4/2004 | Chandrasekaran et al. |
| 2004/0073171 | A1 | 4/2004 | Rogers et al. |
| 2004/0076582 | A1 | 4/2004 | DiMatteo et al. |
| 2004/0131863 | A1 | 7/2004 | Belliveau et al. |
| 2004/0171747 | A1 | 9/2004 | Zhong |
| 2004/0199128 | A1 | 10/2004 | Morris et al. |
| 2004/0220534 | A1 | 11/2004 | Martens et al. |
| 2004/0266301 | A1 | 12/2004 | Vedula et al. |
| 2005/0010275 | A1 | 1/2005 | Sahatjian et al. |
| 2005/0013988 | A1 | 1/2005 | Fu et al. |
| 2005/0119724 | A1 | 6/2005 | Phaneuf et al. |
| 2005/0131356 | A1 | 6/2005 | Ash et al. |
| 2005/0182352 | A1 | 8/2005 | DiMatteo et al. |
| 2005/0192546 | A1 | 9/2005 | Griego et al. |
| 2005/0216074 | A1 | 9/2005 | Sahatjian et al. |
| 2006/0004325 | A1 * | 1/2006 | Hamatake et al. ........ 604/43 |
| 2006/0052757 | A1 | 3/2006 | Fischer et al. |
| 2006/0189922 | A1 * | 8/2006 | Amarasinghe et al. ...... 604/28 |
| 2007/0299043 | A1 | 12/2007 | Hunter et al. |
| 2008/0108975 | A1 * | 5/2008 | Appling et al. ........ 604/532 |
| 2008/0234659 | A1 | 9/2008 | Cheng et al. |
| 2009/0036768 | A1 | 2/2009 | Seehusen et al. |
| 2009/0171319 | A1 | 7/2009 | Guo et al. |
| 2009/0171436 | A1 | 7/2009 | Casanova et al. |
| 2009/0326560 | A1 | 12/2009 | Lampropoulos et al. |

FOREIGN PATENT DOCUMENTS

| | | |
|---|---|---|
| EP | 0328421 | 8/1989 |
| EP | 0589577 | 3/1994 |
| EP | 0987042 | 3/2000 |
| FR | 2718969 | 10/1995 |
| JP | 2001172848 | 6/2001 |
| JP | 2001340466 | 12/2001 |
| JP | 2003037632 | 2/2003 |
| JP | 2006296694 | 11/2006 |
| WO | WO-96/41649 | 12/1996 |
| WO | WO-97/10858 | 3/1997 |
| WO | 99/38550 | 8/1999 |
| WO | 99/42156 | 8/1999 |
| WO | WO-00/53253 | 9/2000 |
| WO | WO-01/70324 | 9/2001 |
| WO | WO-2006/058042 | 6/2006 |

OTHER PUBLICATIONS

Carbothane MSDS from msds.carboline.com accessed Thursday Aug. 4, 2011. http://msds.carboline.com/website/carbmsds.nsf%28a11%29/87496753746CA5888525705A00 4343CE8/$file/Carbothane+134+HG+PDS+3-11.pdf.

International Search Report and Written Opinion mailed Jan. 26, 2009 for International Application No. PCT/US2008/080519 (7 pages).

International Preliminary Report on Patentability mailed Apr. 20, 2010 for International Application No. PCT/US2008/080519 (6 pages).

"AgION's Silver Copper Zeolite Okayed by FDA for Food Contact," AgION Technologies, Inc., http://www.agion-tech.com/NewsDetail.asp?PressID=91, 2 pages (2005).

"Anatomy and Placement," http://www.rnceus.com/picc/piccanat.html, 2 pages (2005).

"Application Guide," Spire Corporation, http://www.spirebiomedical.com/Biomedical/app_guide.html, 3 pgs (2005).

"Biocompatibles—Advanced Biomedical Polymers," http://www.pharmaceutical-technology.com/contractors/drug_delivery/biocompatibles, 3 pages (2005).

"Broviac Catheters, PICC Lines and Other Catheters," The American Pediatric Surgical Association, http://www.eapsa.org/parents/catheter.htm, 13 pages (2005).

"Central Venous Catheters," http://academic.luzerne.edu/nfrusciante/nur204/powerpoints/cvc.pdf, 11 pages (2005).

"Description of Ion Beam Assisted Deposition Process," Spire Corporation, http://www.spirebiomedical.com/Biomedical/ionbeam.html, 2 pages (2005).

"Description of Ion Implantation Process," Spire Corporation, http://www.spirebiomedical.com/Biomedical/ionimpl.html, 4 pages (2005).

"Echo-Coat Ultrasound Needles," The 2001 Medical Design Excellence Awards, http://www.devicelink.com/expo/awards02/stsbiopolymers.html, 2 pages (retrieved from the internet prior to the filing of the application).

"Electrically Ionized Metals for the Prevention of Catheter Colonization with Microorganisms," The University of Texas MD Anderson Cancer Center, Office of Technology Development, http://www.mdanderson.orq/departments/techcommerc, 2 pages(2005).

"FAQ: Electroplating—How It Works," http://www.finishing.com/faqs/howworks.html, 4 pages (2005).

"Fighting Infections, Healing Wounds," AcryMed, Inc., http://www.acrymed.com, 1 page (2005).

"Flexima™ Tight Loop All-Purpose Drainage Catheters," Boston Scientific Corporation, http://www.bostonscientific.com, 1 page (2005).

Gibbins, "SilvaGard™ Technology Summary," AcryMed, Inc., http://www.acrymed.com/pdf%20files/bpease_silvgrd.pdf, 8 pages (2006).

Gibbins et al., "The Role of Antimicrobial Silver Nanotechnology," Medical Device & Diagnostic Industry, http://www.devicelink.com/mddi/archive/05/08/005.html, 6 pages (2005).

"Ion Beam Processing (IBP) Technologies—Sector Study," BDM Federal Inc., prepared for the North American Technology and Industrial Base Organization (NATIBO), 133 pages (1996).

"Ion-Sight™," Spire Corporation, http://www.spirebiomedical.com/Biomedical/Ionsight.html, 2 pages (2005).

"Ion-Sight™ Radio-Opaque Coatings for Medical Devices is a State-of-the-Art Metallic Coating Applied to Polymers," 1 page (retrieved from the internet prior to filing of the application).

Management of a PICC Line (Peripherally Inserted Central Catheter), CancerBACUP, http://www.cancerbacup.org.uk/Treatments/Chemotherapy/Linesports/PICCline, 4 pages (2005).

"New Multifunctional Textiles: Antimicrobial Treatments," Intelligent Textile Structures—Application, Production & Testing, International Workshop, Thessaloniki, Greece, Amphitheater of Thessaloniki Technology Park, 31 pages (2005).

Oberst, "Researchers Describe How to Put the 'Nano' in Synthetic Polymers," Cornell Chronicle, http://www.news.cornell.edu/Chronicle/04/6.10.04/CCMR-POP_conf.html, 2 pages (2004).

"ON-Q C-Bloc Continuous Nerve Block System," I-Flow Corporation, http://www.iflo.com/prod_ong_classic.php, 7 pages (2005).

"ON-Q® PainBuster® Post-Op Pain Relief System," I-Flow Corporation, http://www.iflo.com/prod_ong_classic.php, 7 pages (2005).

Powers, "Antimicrobial Silver Nanoparticles Eliminate Biofilm Formation on Medical Devices," NanoBiotech News, vol. 3, No. 30, 2 pages (2005).

"Process Services," Spire Corporation, http://www.spirebiomedical.com/Biomedical/process_serv.html, 2 pages (2005).

Rosenthal, "PICC Line," University of Illinois Medical Center at Chicago, http://uimc.discoveryhospital.com/main.php?t=enc&id=3017, 2 pages (2005).

"SilvaGard™ Antimicrobial Surface Treatment," AcryMed, Inc., http://www.acrymed.com/techATD.htm, 2 pages (2005).

"Silver Catheter Destroys Bacterial Paradise," NewsDesk No. 9820, Siemens AG, http://w4.siemens.de/en2/html/press/newsdesk_archive/1998/e_9820_d.html, 2 pages (1998).

Sobie, "*Ion Beam Technology for Thin Film Applications*," edited from a reprint of Vacuum & Thinfilm, 6 pages (2001).

"SPI-Argent™," Spire Corporation, http://www.spirebiomedical.com/Biomedical/SPIargent.html, 2 pages (2005).

"Tal MicroDrainage™ Set," Boston Scientific Corporation, http://www.bostonscientific.com, 2 pages (2005).

"Technology Overview," Spire Corporation, http://www.spirebiomedical.com/Biomedical/techoverview.html, 1 page (2005).

"Types of CV ADs," Hemophilia Galaxy, http://www.hemophiliagalaxy.com/patients/managinci/va_central/types.html, 3 pages (2005).

"Vaxcel® Implantable Ports with PASV® Valve Technology," Boston Scientific Corporation, http://www.bostonscientific.com, 3 pages (2005).

"Vaxcel® Implantable Ports with PASV® Valve Technology—Port Design Options," Image, Boston Scientific Corporation, http://www.bostonscientific.com (2005).

"Vaxcel® Peripherally Inserted Central Catheter (PICC)," Boston Scientific Corporation, http:www.bostonscientific.com, 3 pages (2005).

"Vaxcel® Peripherally Inserted Central Catheter (PICC)—Instructions for Use," Boston Scientific Corporation, http://www.bostonscientific.com, 3 pages (2005).

"Vaxcel® Peripherally Inserted Central Catheter (PICC)—Product Information" Boston Scientific Corporation, http://www.bostonscientific.com, 3 pages (retrieved from the internet prior to the filing of the application).

"Vaxcel® Plus Chronic Dialysis Catheter," Boston Scientific Corporation, http://www.bostonscientific.com, 2 pages (2005).

"Vaxcel® Tunneled Central Venous Catheter," Boston Scientific Corporation, http://www.bostonscientific.com, 5 pages (2005).

"Vaxcel® Tunneled Central Venous Catheters—Product Information," Boston Scientific Corporation, http://www.bostonscientific.com, 3 pages (retrieved from the internet prior to filing of the application).

"Venous Access Device Insertion and Maintenance," Boston Scientific Corporation, http://www.bostonscientific.com/templatedata/imports/HTML/infusion_therapy/index.html, 1 page (2005).

Zschaler, "Testing of the Antimicrobial Effect of Catheter Tubing with a Roll Culture Method," 4 pages (2005).

Hunter et al., "Anti-Scarring Drug Combinations and Use Thereof," U.S. Appl. No. 60/723,053 Specification (2005).

J.A. Zawacki, "Carbothane Fixed Split-Tip Dialysis Catheters for Longer-Term Haemodialysis," Business Briefing: Global Healthcare—Advanced Medical Technologies, pp. 1-2 (2004).

Thermedics Polymer Products,"Committed to Providing Medical Grade Thermoplastic Polyurethane Resins," http://www.viasys.tv/prod_serv/downloads/139_Brochure.pdf, pp. 1-8 (2005).

"HemoSplit Catheter, 510(k), Summary of Safety and Effectiveness, 21 CFR 807.92(a)," (2003).

"Noveon, Medical Urethanes," http://www.estane.com/technology/Medical.asp, pp. 1-6 (2005).

"Vaxcel® Plus Chronic Dialysis Catheter," http://www.bostonscientific.com/med_specialty/deviceDetail.jsp?task=tskBasicDevice.jsp&sectionId=4&re1ID=4,178,179,180&deviceId=13015&uniqueId=MPDB3839, (2007).

T.M. Vesely, "Tunneled Catheter Design: Does it Matter? (Lecture)," The Journal of Vascular Access, vol. 6, pp. 132-136 (2005).

Asch, "Venous access: options, approaches and issues," Can Assoc. Radiol J., vol. 52, No. 3 pp. 153-164 (2001).

Herts et al., "Power injection of contrast media using central venous catheters: feasibility, safety, and efficacy," AJR Am. J. Roentgenol., vol. 176, No. 2, pp. 447-453 (2001).

Roth et al., "Influence of radiographic contrast media viscosity to flow through coronary angiographic catheters," Cathet. Cardiovasc. Diagn., vol. 22, No. 4, pp. 290-294 (1991).

Carlson et al., "Safety considerations in the power injection of contrast media via central venous catheters during computered tomogrphic examinations," Invest. Radiol., vol. 27, No. 5, p. 337-340 (1992).

Kaste et al., "Safe use of powr injectors with central and peripheral venous access devices for pediatrict CT," Pediatr. Radiol., vol. 26, No. 8, pp. 449-501 (1996).

Herts et al., "Power injection of intravenous contrast material through central venous catheters for CT: in vitro evaluation," Radiology, vol. 200, No. 3, pp. 731-735 (1996).

Rivitz et al., "Power injection of peripherally inserted central catheters," J. Vasc. Interv. Radiol., vol. 8, No. 5, pp. 857-863 (1997).

Rogalla et al., Safe and easy power injection of contrast material through a central line, Eur. Radiol., vol. 8, No. 1, pp. 148-149 (1998).

Williamson et al., "Assessing the adequacy of peripherally inserted central catheters for power injection of intravenous contrast agents for CT," J. Comput. Assist. Tomogr., vol. 25, No. 6, pp. 932-937 (2001).

Chahoud et al., "Randomized comparison of coronary angiography using 4F catheters: 4F manual versus 'Acisted' power injection technique," Catheter Cardiovasc. Interv., vol. 53, No. 2, pp. 221-224 (2001).

Walsh et al., "Effect of contrast agent viscosity and injection flow velocity on bolus injection pressures for peripheral venous injection in first-pass myocardial perfusion studies," Technol. Health Care, vol. 10, No. 1, pp. 57-63 (2002).

Saito et al., "Diagnostic brachial coronary arteriography using a power-assisted injector and 4 French catheters with new shamps," J. Invasive Cardiol., vol. 9, No. 7, pp. 461-468 (1997).

* cited by examiner

US 8,337,451 B2

RECIRCULATION MINIMIZING CATHETER

PRIORITY CLAIM

This application claims priority to U.S. Provisional Application Ser. No. 60/981,343 entitled "Recirculation Minimizing Catheter," filed on Oct. 19, 2007 and U.S. Provisional Application Ser. No. 60/981,371 entitled "Recirculation Minimizing Catheter," filed on Oct. 19, 2007. The Specifications of the above-identified applications are incorporated herewith by reference.

BACKGROUND

The treatment of chronic disease often involves the use of catheters to simultaneously inject and withdraw fluids from the vascular system. During kidney dialysis, for example, a large amount of blood is withdrawn, treated externally and then returned to the vascular system.

The removal and return of the blood is generally carried out using a catheter and needle assembly with a first lumen aspiring blood from a vein while another returns the treated blood. Inlet and outlet orifices of the assembly are generally spaced from one another to minimize recirculation of the returned blood into the inlet orifice.

SUMMARY OF THE INVENTION

In one aspect, the present invention is directed to a flow control tip for a catheter comprising a partition dividing the catheter into first and second lumens, a first orifice fluidly connected to the first lumen and a second orifice fluidly connected to the second lumen, the first orifice being proximal to the second orifice, an elongate protrusion extending along a portion of the partition substantially along a centerline of the elongated body and a deflecting surface extending at an angle relative to the protrusion to direct flow from the first orifice away from the centerline.

DETAILED DESCRIPTION

Figure 1:
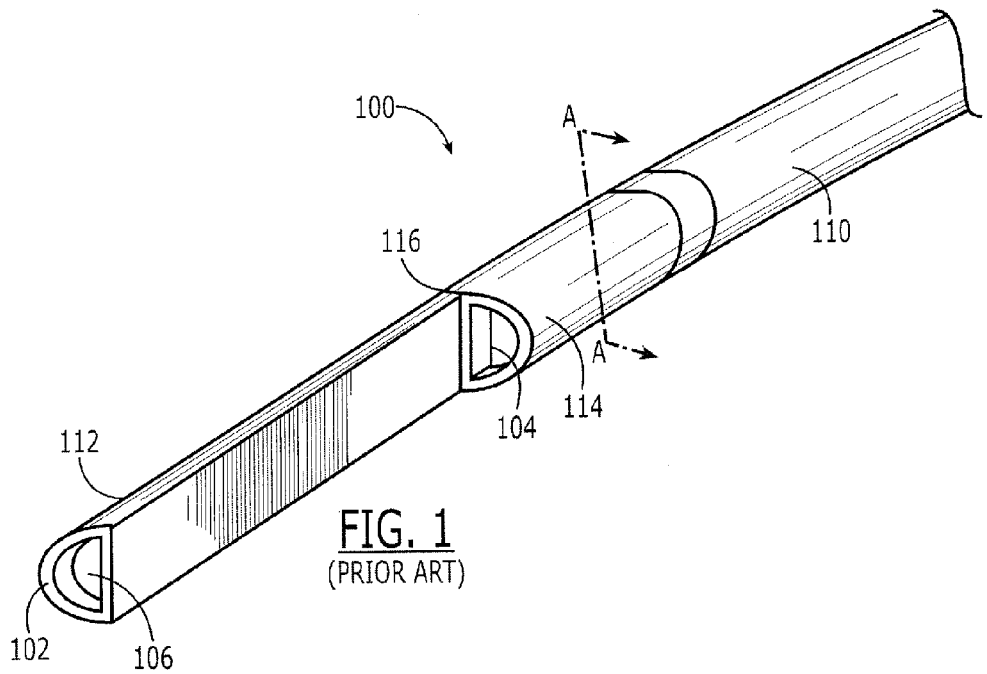
FIG. 1 is a perspective view of a conventional dual lumen catheter.

The present invention may be further understood with reference to the following description and the appended drawings, wherein like elements are referred to with the same reference numerals. The present invention relates to devices for accessing the vascular system and, in particular, to catheters for withdrawing and returning blood during dialysis. More particularly, the invention relates to catheter tips that minimize recirculation during such procedures. However, those of skill in the art will understand that the present invention may also be successfully implemented in other catheter components, such as, for example, catheter side ports.

It is often necessary to reverse the flow through a dialysis catheter so that the outlet orifice temporarily serves as an inlet and the inlet orifice temporarily serves as an outlet. For example, flow may be reversed for a sustained period of time when the wall of a blood vessel becomes attached to the inlet orifice due to the suction applied to aspire blood, or when a sheath of fibrin or a thrombus forms at the inlet reducing blood flow therethrough. In the former instance, flow may be momentarily reversed until the wall of the blood vessel is released from suction. Flow reversal may be performed during a single or multiple medical procedures. As these catheters are generally designed for the standard flow mode (i.e., aspiration into a first orifice optimized as an inlet and outflow from a second orifice optimized as an outlet), the geometry of the distal tip is imperfectly adapted to reverse flow and recirculation tends to increase during reverse flow.

Exemplary embodiments of the present invention provide a dual lumen catheter tip reducing recirculation in various modes of operation while reducing manufacturing costs. More specifically, tips for multi-lumen catheters according to the invention are manufactured using extrusion techniques such as, for example, skiving, drilling, heat-forming and RF tipping to obtain profiles that reduce recirculation in the normal and reverse modes of operation. As the exemplary tips may be formed without the need to join separate bodies (e.g., by bonding a molded tip to a separate structure) manufacturing costs are reduced.

Figure 2:
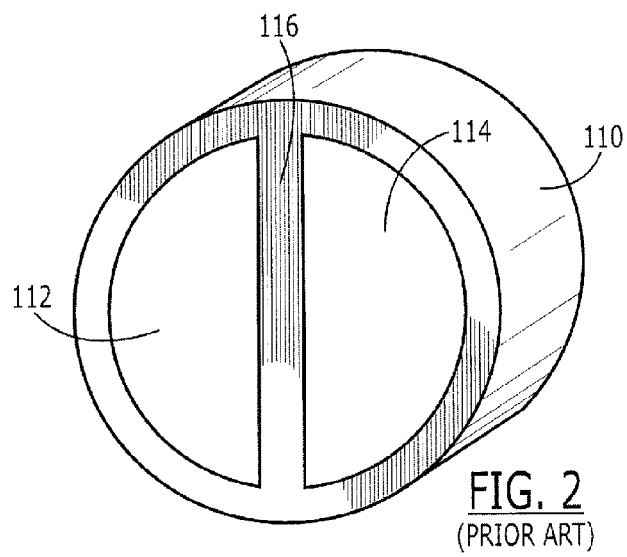
FIG. 2 is a cross-section of the catheter of FIG. 1 taken along line A-A.

FIGS. 1 and 2 show a conventional dual lumen catheter 100 (e.g., a Vaxcel® Plus dialysis catheter) comprising an elongate body defining first and second lumens 112, 114, respectively, separated by a partition 116. A substantially cylindrical outer wall 110 surrounds both lumens 112, 114 and provides structural integrity to the catheter 100. The distal tip 102 of the catheter 100 comprises a first orifice 104 in fluid connection with the lumen 114 and, staggered from the first orifice 104, a second orifice 106 in fluid connection with the lumen 112. In the normal mode of operation the first lumen 112 and the first orifice 104 function as inlets for the aspiration of blood while the second lumen 114 and the second orifice 106 function as outlets for blood returning from dialysis treatment. As would be understood by those skilled in the art, the roles of the orifices 104, 106 and the lumens 112, 114 are reversed during the reverse mode of operation.

Three-dimensional computational fluid dynamics models have been utilized to shape the tips according to the invention. Pressure and velocity flow values derived from cardiac pulses were modeled to evaluate the performance of the tips and the results were averaged over time to derive representative results. The worst case recirculation values are illustrated by models shown in the accompanying drawings.

Figure 3:
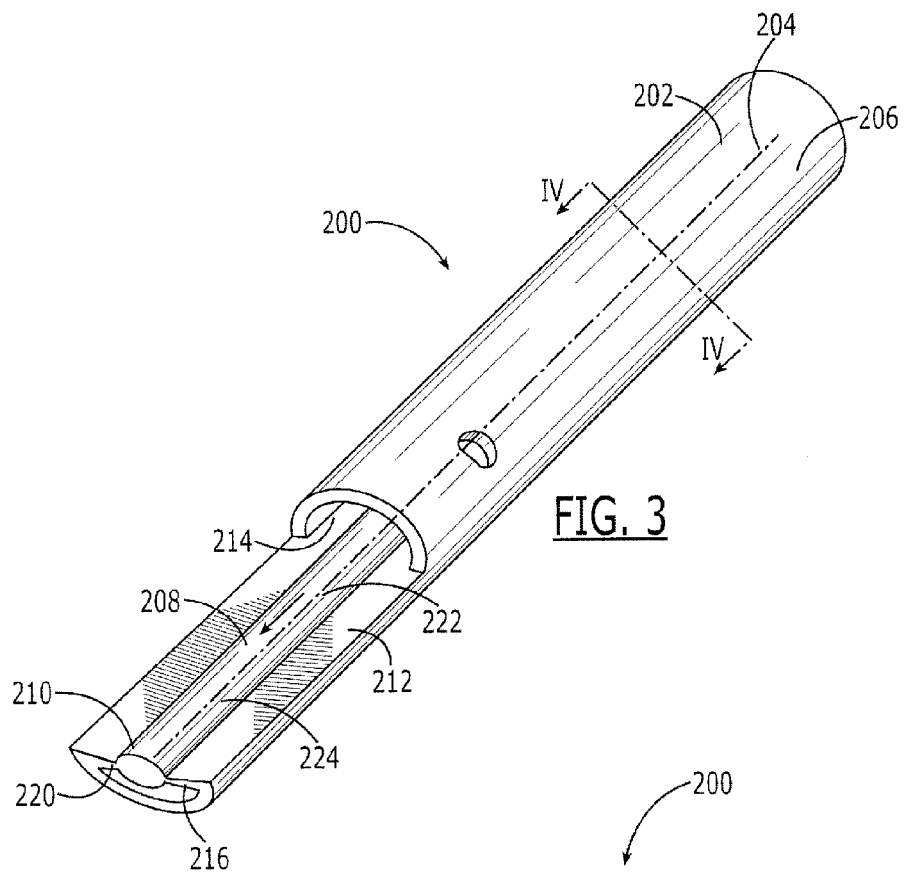
FIG. 3 is a perspective view of a catheter according to an embodiment of the present invention.
Figure 4:
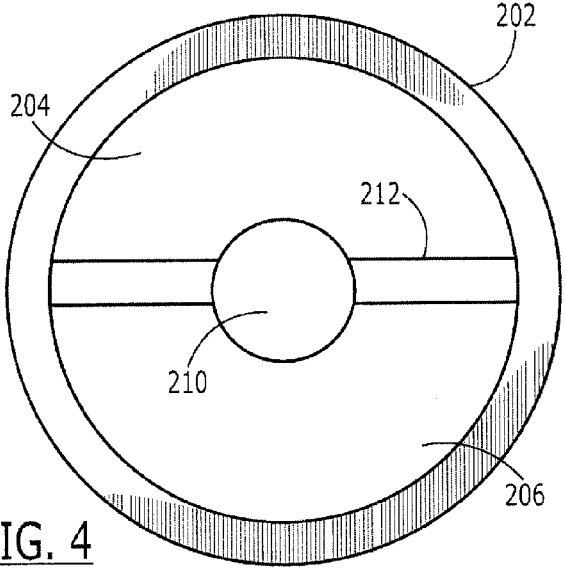
FIG. 4 is a cross-sectional view of the catheter of FIG. 3 taken along line IV-IV.

As shown in FIGS. 3 and 4, a catheter tip 200 according to an exemplary embodiment of the invention comprises an elongated shell 202 including a first lumen 204 which, in the normal mode of operation, aspirates fluid from the vascular system (i.e., an inflow lumen) via a first orifice 214 and a second lumen 206 which, in the normal mode of operation, returns fluid from the catheter tip 200 to the vascular system (i.e., an outflow lumen) via a second orifice 216. The lumens 204 and 206 are separated by a partition 212 extending substantially the length of the tip 200. As the tip 200 is substantially circular, the partition 212 divides the tip 200 to form the lumens 204 and 206 as substantially equal in size and substantially semicircular. Those skilled in the art will understand that if lumens of different size and shape are desired, the placement and/or the shape of the partition 212 may be altered as needed. The shell 202 extends around the tip 200 on one side of the partition 212 to the second orifice 216 and to the first orifice 214 on the other side of the partition 212. As would be understood by those skilled in the art, the tip 200 may be integrally formed as part of a catheter, or may be manufactured separately and then attached to a catheter via any of a variety of conventional attachment methods. It will also be understood that, if desired, the tip 200 may include more than two lumens.

As seen in FIG. 3, the first and second orifices 214, 216 of the tip 200 are offset from one another along a longitudinal axis of the tip 200 and each of the first and second orifices 214, 216, respectively, includes one or more additional features directing outflow therefrom away from the other orifice. As best seen in the cross-section of FIG. 4, a protrusion 210 which, in this embodiment is a substantially cylindrical extrusion with a diameter smaller than an inner diameter of the shell 202 forms a rod extending substantially along a centerline of the partition 212, coaxially with the shell 202. The protrusion 210 extends along substantially the entire length of the shell 202 above the partition 212 in the distal portion 220 of the tip 200, beyond the first orifice 214. In this embodiment, the protrusion 210 is concentric with the shell 202. However, in other embodiments, the protrusion 210 may not be concentric. In addition, the shape of the protrusion 210 need not be circular and in other embodiments, the shape (e.g., triangular, elliptical, etc.) and/or the diameter of the protrusion 210 may be adjusted to suit a particular need (e.g., a desired flow characteristic, flexibility, etc.).

According to the invention, the protrusion 210 comprises a diverting structure 208 which, in this embodiment is formed as a shallow cut positioned approximately half the distance along the longitudinal axis of the tip 200 between the first orifice 214 and the second orifice 216. However, those skilled in the art will understand that the diverting structure 208 may be formed anywhere between the first and second orifices 214, 216, respectively. The diverting structure 208 may be sculpted by, for example, skiving a portion of the protrusion 210 to form a downward sloping diverting structure 222 and an upward sloping diverting structure 224. Alternatively, the diverting structure 208 may be formed by cutting the protrusion 210 along a substantially constant radius. In the reverse mode of operation the protrusion 210 and the diverting structure 208 direct outflow from the outlet orifice 214 upward, away from the longitudinal axis of the tip 200 and the inlet orifice 216. Additional embodiments may include multiple angled cuts formed by a series of skives, compound cuts, or any other method known to those skilled in the art. One or more of the multiple cuts may be angled about a radial axis of the tip 200 to bias flow to side of the tip 200 or to bias portions of the flows in different directions relative to an axis of the tip 200. Thus, the diverting structure 208 may guide the flow laterally relative to the axis of the tip 200 in addition to diversion of the flow radially outward from the axis.

The second orifice 216 is formed at an angle, extending proximally at an acute or, in the alternative, an obtuse, angle from a distal end of the partition 212 which is preferably selected to provide desired flow characteristics to the tip 200. For example, a steeper angle may direct fluid further from the centerline in the reverse mode and draw fluid from further away in the normal mode. Those skilled in the art will understand that this angle may be formed by cutting the tip 200 along a desired plane, by molding, compound cutting, or by any other conventional method.

Figure 5:
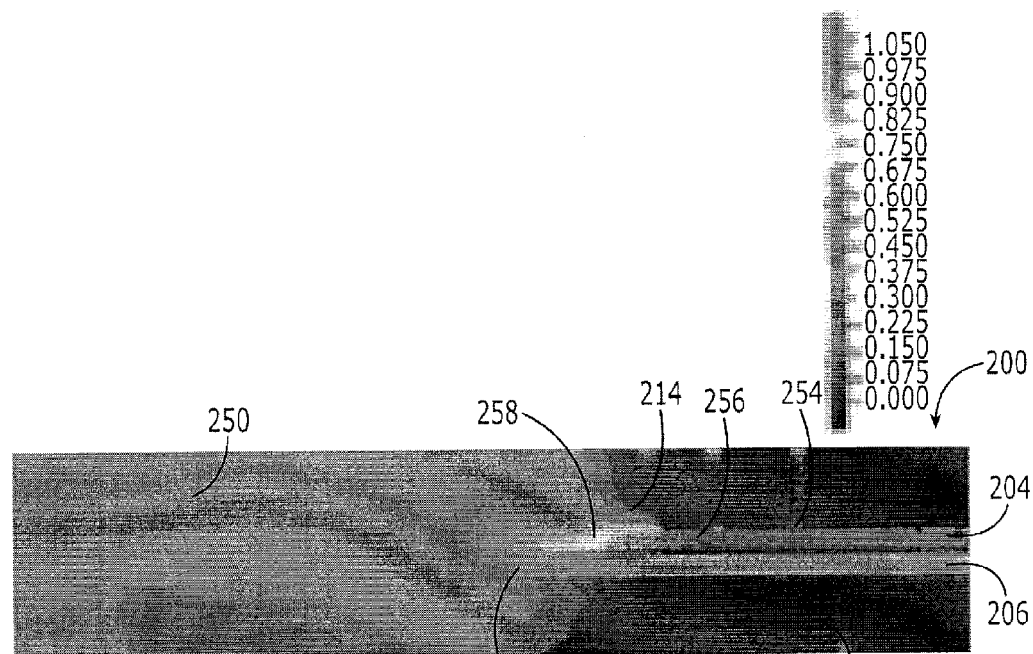
FIG. 5 is a side view of the catheter of FIG. 3 showing a computed flow pattern around a distal tip thereof.

A computational fluid dynamics analysis of the flow generated by the exemplary tip described above in the reverse mode of operation is shown in FIG. 5. As shown in FIG. 5, in the reverse mode of operation, filtered blood 254 flows out of the lumen 204 to exit the tip 200 via the first orifice 214, initially passing over the protrusion 210. However as the flow passes the diverting structure 208, it is pushed away from the centerline of the tip 200 and away from the second orifice 216 as indicated by the transition from section 256 (dark shade of gray) to section 258 (light shade of gray), reducing recirculation. In addition, if radially angled cuts are included in the protrusion 210, the flow is biased to one side (e.g., into the plane of the side view of FIG. 5). As shown in the diagram, unfiltered blood 250 is aspired into the second orifice 216, together with a reduced portion of the filtered blood 254. In the exemplary embodiment, the numerical modeling predicts a recirculation rate of about 15% for the conditions shown in FIG. 5.

Figure 6:
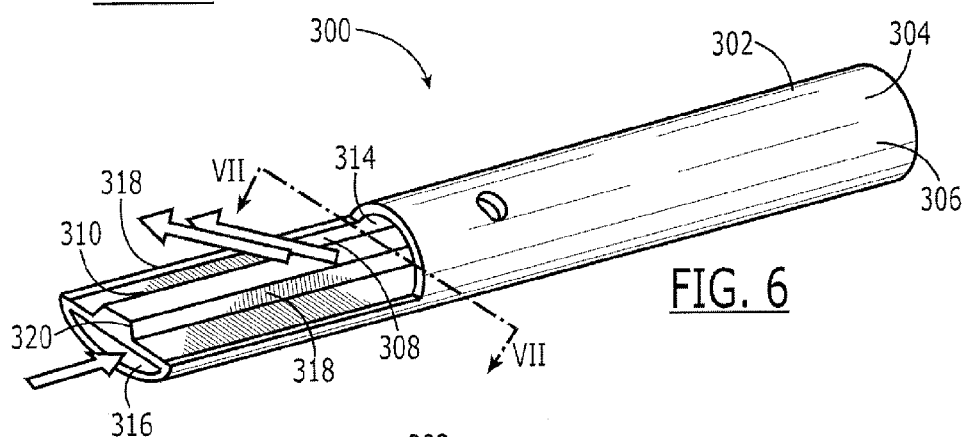
FIG. 6 is a perspective view of a catheter according to an embodiment of the present invention.
Figure 7:
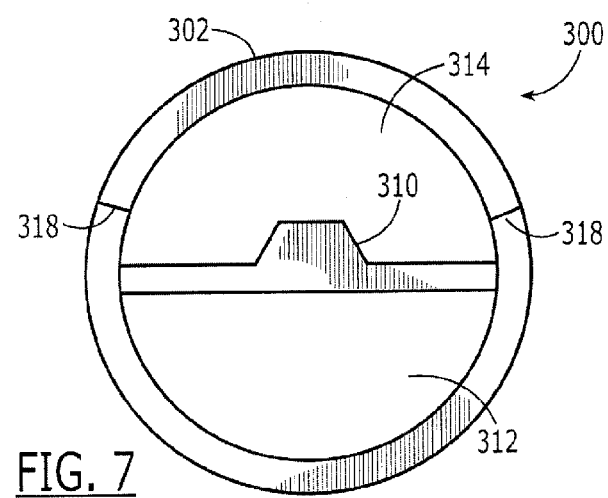
FIG. 7 is a cross-sectional view of the catheter of FIG. 6 taken along line VII-VII.

FIGS. 6 and 7 show a catheter tip 300 according to an exemplary embodiment of the invention. The tip 300 comprises an elongated shell 302 including a first lumen 304 which, in the normal mode of operation, aspirates fluid from the vascular system (i.e., an inflow lumen) via a first orifice 314 and a second lumen 306 which, in the normal mode of operation, returns fluid from the tip 300 to the vascular system (i.e., an outflow lumen) via a second orifice 316. The lumens 304 and 306 are separated by a partition 312 extending substantially the length of the tip 300. The partition 312 divides the tip 300 to form the lumens 304 and 306 as substantially equal in size and substantially semicircular. Those skilled in the art will understand that if lumens of different size and shape are desired, the placement and/or the shape of the partition 312 may be altered as needed. The shell 302 extends around the tip 300 on one side of the partition 312 to the second orifice 316 and to the first orifice 314 on the other side of the partition 312. As would be understood by those skilled in the art, the tip 300 may be integrally formed as part of a catheter, or may be manufactured separately and then attached to a catheter via any of a variety of conventional attachment methods. It will also be understood that the tip 300 may include any plurality of lumens.

As seen in FIG. 6, the first and second orifices 314, 316 of the tip 300 are offset from one another along a longitudinal axis of the tip 300. As best seen in the cross-section of FIG. 7, a protrusion 310 which, in this embodiment is a substantially semi-circular extrusion with a cropped top surface and a diameter smaller than an inner diameter of the shell 302, forming a semi-circular rod extending substantially along a centerline of the partition 312, coaxially with the shell 302. The protrusion 310 extends along substantially the entire length of the shell 302 above the partition 312 in the distal portion 320 of the tip 300, beyond the first orifice 314. The protrusion 310 reduces a cross-sectional size of the lumen 304 and imparts an arch shape thereto while not protruding into the lumen 312 at all. In this embodiment, the protrusion 310 is concentric with the shell 302. However, in other embodiments, the protrusion 310 may not be concentric. In addition, the shape of the protrusion 310 need not be semi-circular and in other embodiments, the shape (e.g., triangular, elliptical, etc.) and/or the radius of the protrusion 310 may be adjusted to suit a particular need (e.g., a desired flow characteristic). The amount of cropping may also be varied to produce a specific height profile for the protrusion 310.

According to the invention, the protrusion 310 comprises a diverting structure 308 which, in this embodiment is formed as a shallow cut approximately half the distance along the longitudinal axis of the tip 300 between the first orifice 314 and the second orifice 316. The diverting structure 308 may be sculpted in a manner similar to that of the diverting structure 208. For example, a downward and/or an upward sloping diverting structure may be formed by skiving, cutting, etc. Additional embodiments may include multiple angled cuts formed by a series of skives, compound cuts, or any other method known to those skilled in the art. One or more of the multiple cuts may be angled about a radial axis of the tip 300 and function to bias flow to one or more sides of the tip 300. Thus, the diverting structure 308 may guide the flow sideways in addition to upwards.

The shell 302 may be sculpted (e.g., skived, cut, etc.) to include a pair of side walls 318 extending between the first orifice 314 and the second orifice 316. The walls 318 may be formed by one or more lengthwise cuts across the tip of the device and may be driven by cross section geometry. As shown in the cross-section of FIG. 7, the walls 318 are angled in an upwardly radial direction. In the exemplary embodiment shown, an inner surface of the walls 318 is curved to match the curvature of an inner surface of the shell 302. However, in other embodiments, the inner surface may be have a different shape, such as a bevel, a rounded edge, etc. that functions to guide the flow upwards, away from the centerline of the tip 300. A height of the walls 318 may be selected to provide a desired flow characteristic. In the exemplary embodiment, the height of the walls 318 is greater than the height of the protrusion 310. However, if a greater amount of fluid diversion is desired, the height of the walls 318 may be increased.

The second orifice 316 is formed at an angle, extending proximally at an acute angle from a distal end of the partition 312. The angle of the second orifice 316 may be selected to provide a desired flow characteristic. For example, a steeper angle may direct fluid further away from the centerline in the reverse mode and draw fluid from further away in the normal mode. Those skilled in the art will understand that this angle may be formed by cutting the tip 300 along a desired plane, by molding, compound cutting, or by any other suitable method.

Figure 8:
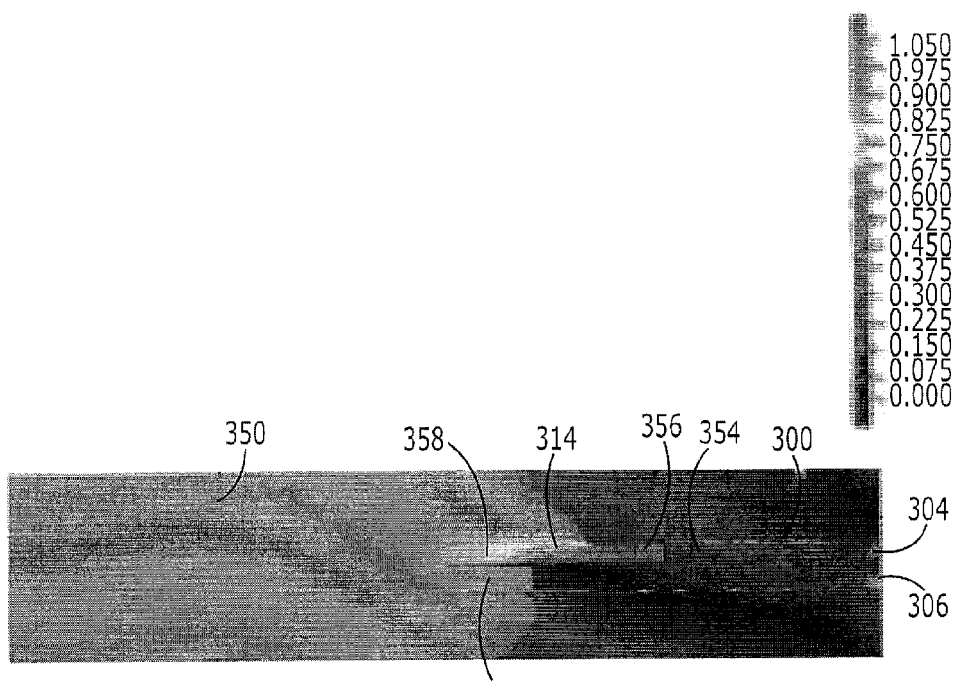
FIG. 8 is a side view of the catheter of FIG. 6 showing a computed flow pattern around a distal tip thereof.

A computational fluid dynamics analysis of the flow generated by the exemplary tip described above in the reverse mode of operation is shown in FIG. 8. As shown in FIG. 8, in the reverse mode of operation, filtered blood 354 flows out of the lumen 304 to exit the tip 300 via the first orifice 314, initially passing over the protrusion 310. However as the flow passes the diverting structure 308, it is pushed away from the centerline of the tip 300 and away from the second orifice 316 as indicated by the transition from section 356 (dark gray) to section 358 (light gray), reducing recirculation. The flow is further directed by the walls 318, the curvature of which guides the flow upwards. In addition, if radially angled cuts are included in the protrusion 310, the flow is biased to one side (e.g., into the plane of the side view of FIG. 8). As shown in the diagram, unfiltered blood 350 is aspired into the second orifice 316, together with a reduced portion of the filtered blood 354. In the exemplary embodiment, the numerical modeling predicts a recirculation rate of about less than 20% in comparison to one another for the conditions shown in FIG. 8.

Figure 9:
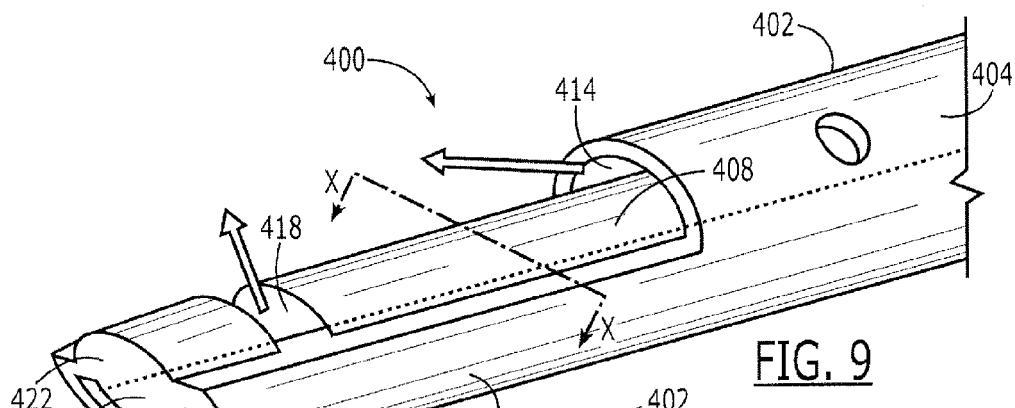
FIG. 9 is a perspective view of a catheter according to an embodiment of the present invention.
Figure 10:
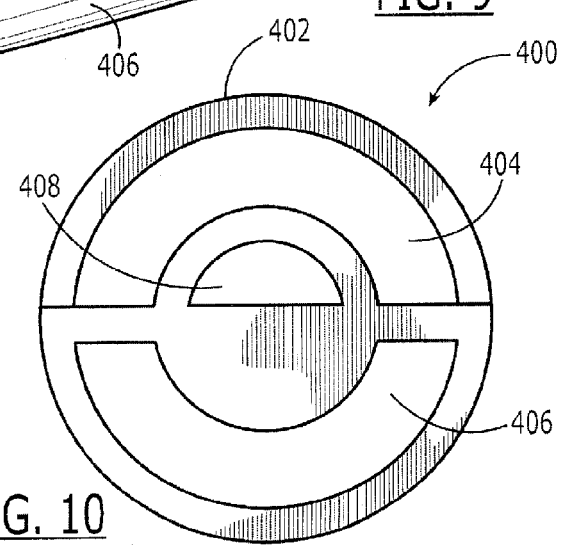
FIG. 10 is a cross-sectional view of the catheter of FIG. 9 taken along line X-X.

FIGS. 9 and 10 show a catheter tip 400 according to an exemplary embodiment of the invention. The tip 400 comprises an elongated shell 402 including a first lumen 404 which, in the normal mode of operation, aspirates fluid from the vascular system (i.e., an inflow lumen) via a first orifice 414 and a second lumen 406 which, in the normal mode of operation, returns fluid from the tip 400 to the vascular system (i.e., an outflow lumen) via a second orifice 416. The lumens 404 and 406 are separated by a partition 412 extending substantially the length of the tip 400. A central portion 422 of the partition 412 is substantially cylindrical and divides the tip 400 to form cross-sections of the lumens 404 and 406 as substantially equal-sized arches. An upper half of the central portion 422 comprises a substantially semi-circular third lumen 408 which, in the normal mode of operation, aspirates fluid via a third orifice 418. As shown in FIG. 9, the third orifice 418 is a radial opening located proximally from a distal end of the tip 400, between the first orifice 314 and the second orifice 316. The third orifice 418 may be formed by, for example, skiving or cutting into the upper half of the central portion 422 until the third lumen 408 is exposed. Lumen 408 may be coupled with lumen 404. A distal wall of the third orifice 418 is angled perpendicularly to a distal end of the upper half of the central portion 422. Thus, distal flow through the lumen 408 is abruptly diverted away from a centerline of the tip 400. However, if a less abrupt angle is desired, the distal wall of the third orifice 418 may be shaped at an acute angle to the distal end of the upper half of the central portion 422.

Those skilled in the art will understand that if lumens of different size and shape are desired, the placement and/or the shape of the partition 412 may be altered as needed. For example, in another embodiment, the partition 412 may be shaped so as to form first and second lumens of different sizes. The shell 402 extends around the tip 400 on one side of the partition 412 to the second orifice 416 and to the first orifice 414 on the other side of the partition 412. As would be understood by those skilled in the art, the tip 400 may be integrally formed as part of a catheter, or may be manufactured separately and then attached to a catheter via a conventional attachment method.

As seen in FIG. 9, the first and second orifices 414, 416 of the tip 400 are offset from one another along a longitudinal axis of the tip 400. As best seen in the cross-section of FIG. 10, the third lumen 408 extends along a centerline of the partition 412, substantially along the entire length of the shell 402. It will be understood by those skilled in the art that the shape and/or position of the third lumen 408 may be altered in other embodiments. For example, in one embodiment, the third lumen 408 may be substantially circular and concentric with the shell 402. In other embodiments, the tip 400 may not be limited to three lumens. For example, a lower portion of the partition 412 may comprise a fourth lumen which, in the normal mode, may function as an outflow or inflow lumen.

The second orifice 416, along with a lower half of a distal end of the central portion 422, are formed at an angle, extending proximally at an acute angle from the distal end of the upper half of the central portion 422. The angles of the second orifice 416 and the lower half of the central portion 422 may be selected to provide a desired flow characteristic. For example, a steeper angle may direct fluid further away from the centerline in the reverse mode and draw fluid from further away in the normal mode. Those skilled in the art will understand that the angles may be formed by cutting the tip 400 along a desired plane, by molding, compound cutting, or by any other suitable method. As seen in FIG. 9, the angle of the second orifice 416 and the angle of the lower half are the same. However, in other embodiments, the angles may not match and may be formed by, for example, a series of cuts oriented at different angles.

Figure 11:
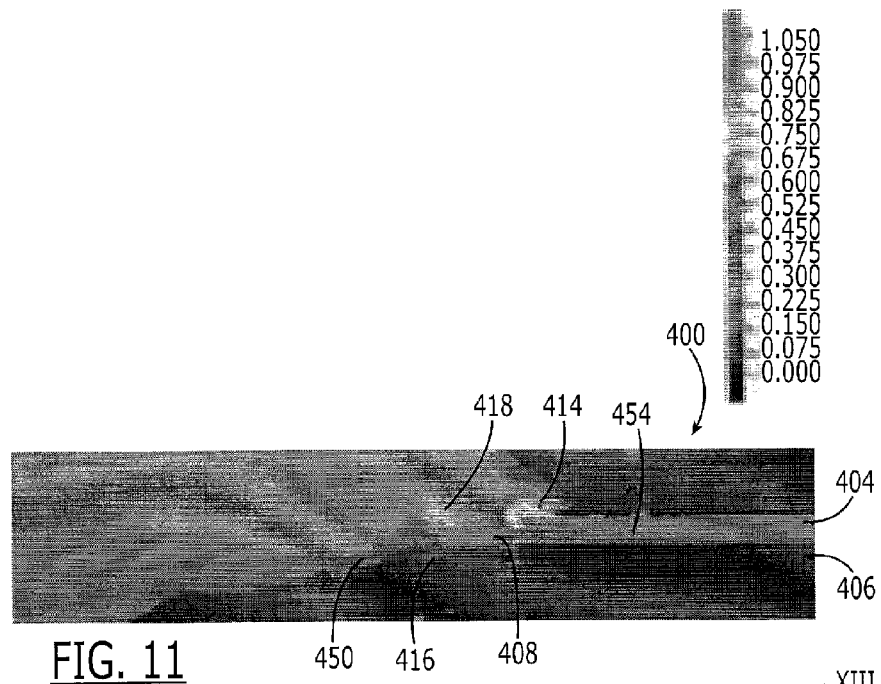
FIG. 11 is a side view of the catheter of FIG. 9 catheter of FIG. 2 showing a computed flow pattern around a distal tip thereof.

A computational fluid dynamics analysis of the flow generated by the exemplary tip described above in the reverse mode of operation is shown in FIG. 11. As shown in FIG. 11, in the reverse mode of operation, filtered blood 454 flows simultaneously out of the lumens 404 and 408. Blood flow out of the lumen 404 is radially dispersed upon reaching the first orifice 414. A remainder of the flow travels through the lumen 408 until reaching a distal wall thereof and being forced upward, away from the centerline of the tip 400. The upward flow is mixed with a portion of the radially dispersed flow, which has traveled distally to reach the third orifice 418. The combined flow has a net upwards direction of travel, away from the centerline of the tip 400. As shown in the diagram, unfiltered blood 450 is aspired into the second orifice 416, together with a reduced portion of the filtered blood 454. In the exemplary embodiment, the numerical modeling predicts a recirculation rate of about less than 15% for the conditions shown in FIG. 11.

Figure 12:
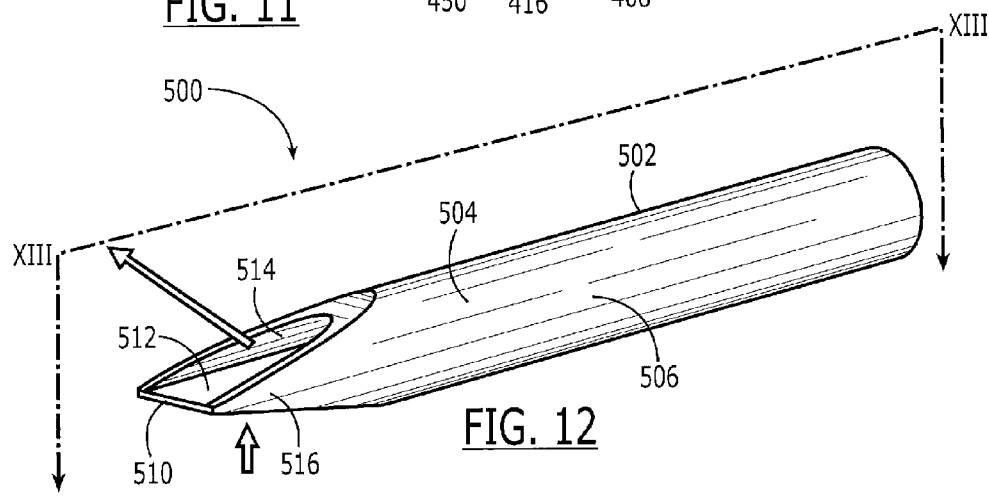
FIG. 12 is a perspective view of a catheter according to another embodiment of the present invention.
Figure 13:
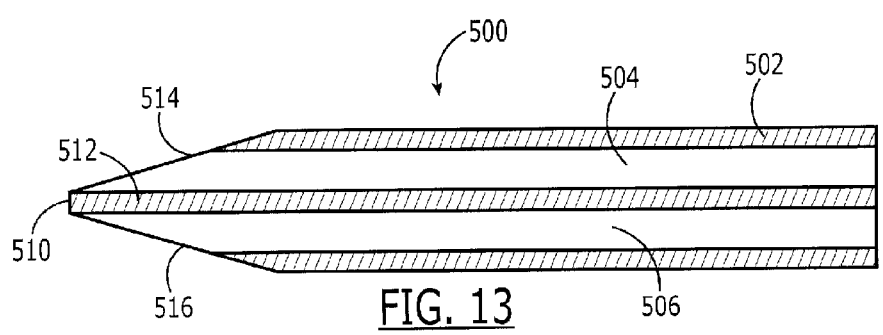
FIG. 13 is a cross-sectional view of the catheter of FIG. 12 taken along line

As shown in FIGS. 12 and 13, a catheter tip 500 according to an exemplary embodiment of the invention comprises an elongated shell 502 including a first lumen 504 which, in the normal mode of operation, aspirates fluid from the vascular system (i.e., an inflow lumen) via a first orifice 514 and a second lumen 506 which, in the normal mode of operation, returns fluid from the catheter tip 500 to the vascular system (i.e., an outflow lumen) via a second orifice 516. The lumens 504 and 506 are separated by a partition 512 extending substantially the length of the tip 500. As the tip 500 is substantially circular, the partition 512 divides the tip 500 substantially along the centerline of the tip 500 to form the lumens 504 and 506 with cross-sectional areas substantially equal to one another and with partially circular or D-shaped cross-sectional shapes. However, those skilled in the art will understand that if lumens of different size and shape are desired, the placement and/or the shape of the partition 512 may be altered as needed. The shell 502 extends around the tip 500 on one side of the partition 512 to the second orifice 516 and to the first orifice 514 on the other side of the partition 512. As would be understood by those skilled in the art, the tip 500 may be integrally formed as part of a catheter, or may be manufactured separately and then attached to a catheter via any of a variety of conventional attachment methods. It will also be understood that the tip 500 may more than two lumens.

As seen in FIG. 12, the first and second orifices 514, 516 are located adjacent to one another at a distal end 510 of the tip 500 on opposite sides of the partition 512. Each orifice 514, 516 is oriented at an acute angle extending proximally from the distal end 510 and may be formed by skiving, compound cutting, or any other method known to those skilled in the art. The angles contribute to an offset distance between the distal end 510 and a proximal end of the orifices 514, 516. If a greater offset (i.e., a larger orifice) is desired, the angles may be adjusted to be more acute. Likewise, less acute angles will form a smaller offset distance. In other embodiments, the orifices 514, 516 may include additional angles such as an inward or outwardly sloping angle which may be formed using the same methods as those used to create the orifices 514, 516 (e.g., skiving, cutting, etc.). In addition, the orifices 514, 516 need not be planar. That is, the angle between an edge of one or both of the orifices 514, 516 may vary from the distal end 510 to a proximal end of the orifice. According to this embodiment, each of the orifices 514, 516 is formed at an angle of approximately 30° relative to the partition 512. However, the angles may be any acute angle and may be different from one another. The angles are preferably in the range between 85° and 10°. However, those skilled in the art will recognize that the angles selected within this range on various desired design features of the catheter.

The orifices 514, 516 in this embodiment are substantially symmetrical with respect to the partition 512. However, in other embodiments the orifices 514, 516 may be oriented at different angles (i.e., asymmetrically). As described above, the orifices 514, 516 function to guide the flow of fluid into and out of the lumens 504, 506. In the reverse mode of operation, the orifice 516 provides a large surface area from which to draw fluid proximally into the lumen 506. In addition, the angle of the second orifice 516 functions to draw fluid separated from the tip 500 in a direction oriented radially away from the centerline of the tip 500. The first orifice 514 functions in a manner similar to that of the second orifice 216 in the normal and reverse modes. These embodiments may feature side skiving to bias the flow laterally away from the centerline of the tip 500.

Figure 14:
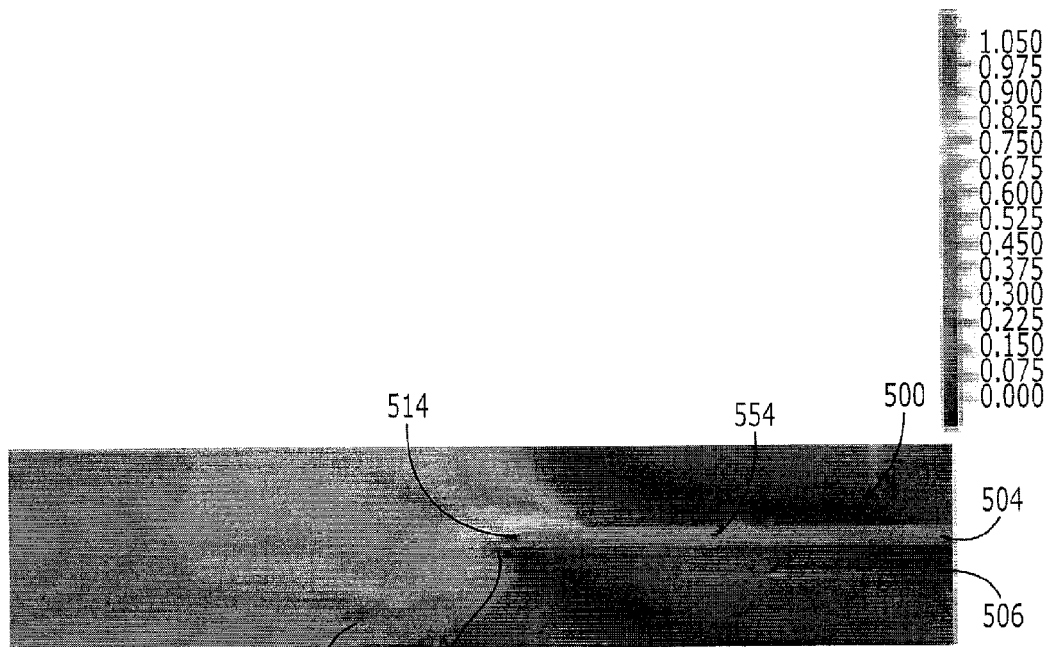
FIG. 14 is a side view of the catheter of FIG. 12 showing a computed flow pattern around a distal tip thereof.

A computational fluid dynamics analysis of the flow generated by the tip 500 in the reverse mode of operation is shown in FIG. 14. As shown in FIG. 14, in the reverse mode of operation, filtered blood 554 flows out of the lumen 504 to exit the tip 500 via the first orifice 514 while unfiltered blood 550 is aspired into the second orifice 516. When the blood 554 reaches the proximal end of the orifice 514, the angle of the orifice 514 disperses the blood radially away from the centerline of the tip 500 while also directing the flow distally away from the distal end 510 of the tip 500. Thus, a majority of the blood 554 is directed away from the centerline of the tip 500 before reaching the distal end 510. Because the second orifice 516 is located on the opposite side of the partition 512, an amount of filtered blood 554 drawn therethrough into the lumen 506 is reduced. In the exemplary embodiment, the numerical modeling predicts a recirculation rate of about 5% for the conditions shown in FIG. 13. The symmetry of the tip 500 enables a similar recirculation rate in the normal mode of operation. That is, the recirculation rate of blood aspired into the first orifice 514 in the normal mode of operation is also approximately 5%.

Figure 15:
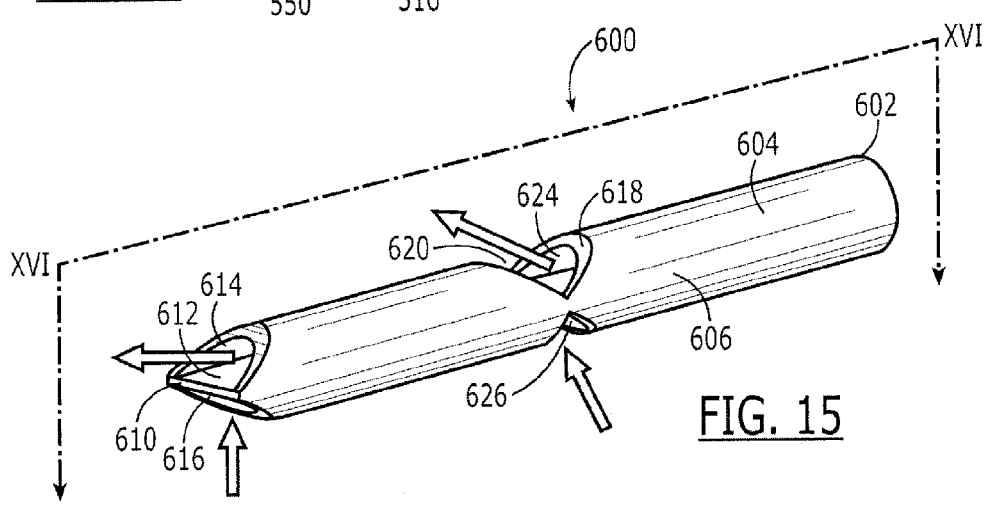
FIG. 15 is a perspective view of a catheter according to an embodiment of the present invention.
Figure 16:
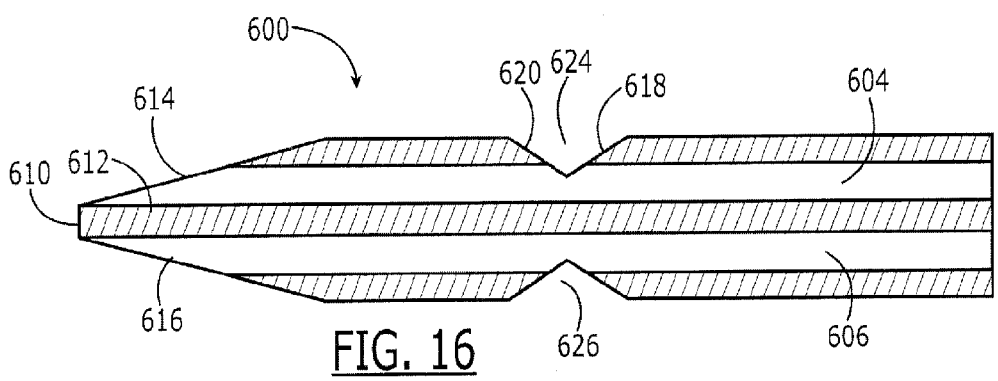
FIG. 16 is a cross-sectional view of the catheter of FIG. 15 taken along line XVI-XVI.

As shown in FIGS. 15 and 16, a catheter tip 600 according to a further exemplary embodiment of the invention comprises an elongated shell 602 including a first lumen 604 which, in the normal mode of operation, aspirates fluid from the vascular system (i.e., an inflow lumen) via a first orifice 614 and a second lumen 606 which, in the normal mode of operation, returns fluid from the tip 600 to the vascular system (i.e., an outflow lumen) via a second orifice 616. The lumens 604 and 606 are separated by a partition 612 extending substantially the length of the tip 600. The partition 612 divides the tip 600 to form the lumens 604 and 606 of substantially equal size and of substantially similar partially circular or D-shaped cross-sections. Those skilled in the art will understand that if lumens of different size and shape are desired, the placement and/or the shape of the partition 612 may be altered as needed. The shell 602 extends around the tip 600 on one side of the partition 612 to the second orifice 616 and to the first orifice 614 on the other side of the partition 612. As would be understood by those skilled in the art, the tip 600 may be integrally formed as part of a catheter, or may be manufactured separately and then attached to a catheter via any of a variety of conventional attachment methods. It will also be understood that the tip 600 may include more than two lumens.

The first and second orifices 614, 616 of the tip 600 are substantially similar to the first and second orifices 514, 516 of the tip 500, located adjacent to one another on opposite sides of the partition 612, and extend proximally from the distal end 610 at acute angles (e.g., 30 degrees from a longitudinal axis of the tip 600) relative to the partition 612. Those skilled in the art will understand that the angle of the orifices 614, 616 relative to the partition 612 may vary in the same range described above for the orifices 514, 516.

As seen in FIG. 15, the tip 600 includes a third orifice 624 and a fourth orifice 626, which are respectively and fluidly coupled to the lumens 604 and 606. Thus, the third and fourth orifices 624, 626 function as additional ports for the inflow and outflow of fluid. The third and fourth orifices 624, 626 are located proximally of the distal end 610. Those skilled in the art will understand that the various distances between the first and second and third and fourth orifices 624, 626, respectively, may vary depending on the size of the catheter and the characteristics of the expected environment in which the catheter is to be deployed. As best seen in the cross-section of FIG. 16, the third and fourth orifices 624, 626 comprise substantially notched openings formed by the intersection of two angled planes cut into the shell 602 and intersecting at a line separated from the partition 612 by a distance selected to leave a portion of the shell 602 extending around a portion of the lumens 604, 606. For example, the walls 618, 620 may intersect at points separated from the partition 612 by a height which will vary depending on the desired design characteristics and expected use of the catheter. The orifices 624, 626 may be formed by, for example, skiving the shell 602 to form proximal and distal walls 618 and 620 of the orifices at acute angles extending in the proximal and distal directions, respectively. In the exemplary embodiment, the proximal and distal walls 618, 620 are substantially symmetrical. However, in other embodiments, the walls 618, 620 may be oriented at different angles (i.e., asymmetrically) with respect to the partition 612. As described above in regard to the other embodiments of the invention, the orifices 614, 616 may be formed with curved walls 618, 620. In addition, the angles formed between the wall 618 and the partition 612 and that formed between the wall 620 and the partition 612 are preferably greater than the angle between the orifice 614 and the partition 612 so that the orifice 614 has a larger opening than the orifice 624. The size and shape of 624 and 626 are preferably chosen to allow the drawing of blood from the most proximal orifice while the momentum of the returning blood carries the bulk of the flow past 624 (or 626) to the tip.

Figure 17:
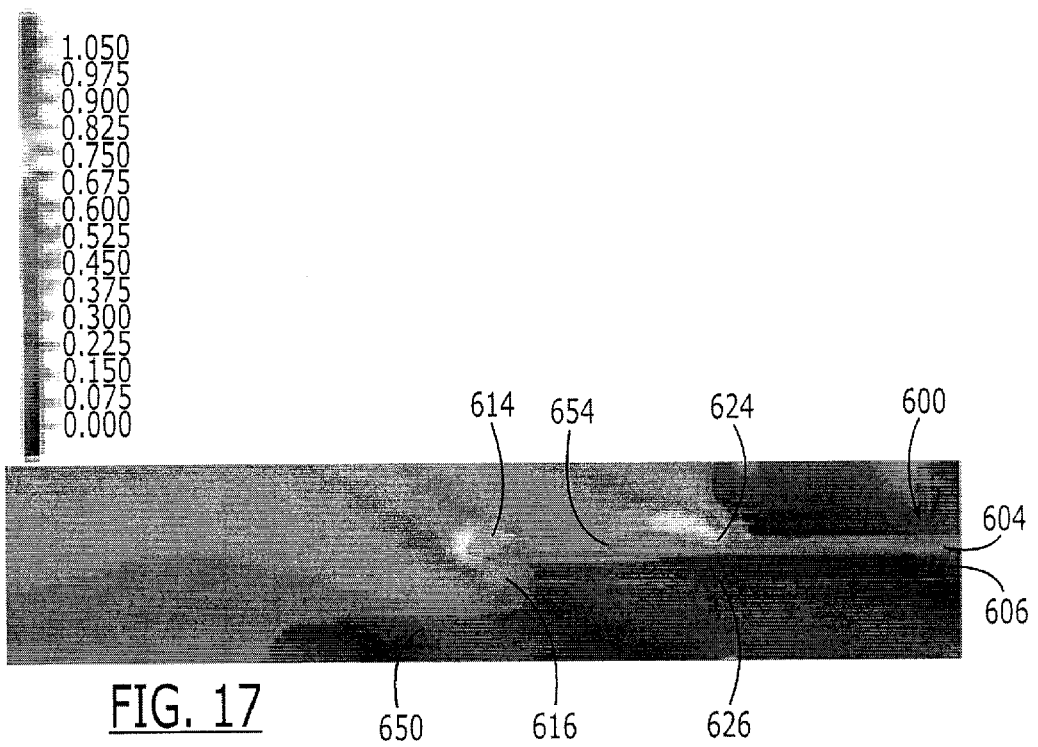
FIG. 17 is a side view of the catheter of FIG. 15 showing a computed flow pattern around a distal tip thereof.

A computational fluid dynamics analysis of the flow generated by the tip 600 in the reverse mode of operation is shown in FIG. 17. As shown in FIG. 17, in the reverse mode of operation, filtered blood 654 flows out of the lumen 604 to exit the tip 600 via the third orifice 624. A remaining portion of the filtered blood 654 travels distally through the first lumen 604 to exit via the first orifice 614. Blood 654 exiting the first and third orifices 614, 624 is dispersed radially away from the centerline of the tip 600 while flowing distally away from the orifices 614, 624. As shown in the diagram, unfiltered blood 650 is aspired into the second orifice 616 and the fourth orifice 626, together with a reduced portion of the filtered blood 654. The fourth orifice 626 is closer to a pulling force of the second lumen 606 and thus, receives a majority of the blood drawn into the second lumen 606. Furthermore, because the fourth orifice 626 is located on the opposite side of the partition 612 from the third orifice 624 and is located proximally of the distal end 610, the blood drawn therein is almost entirely comprised of unfiltered blood 650. Likewise, a majority of the filtered blood 654 exits via the third orifice 624 while a small portion of the filtered blood 654 mixes with the unfiltered blood 650 at the distal end 610. In the exemplary embodiment, the numerical modeling predicts a recirculation rate of about 3% for the conditions shown in FIG. 17.

Figure 18:
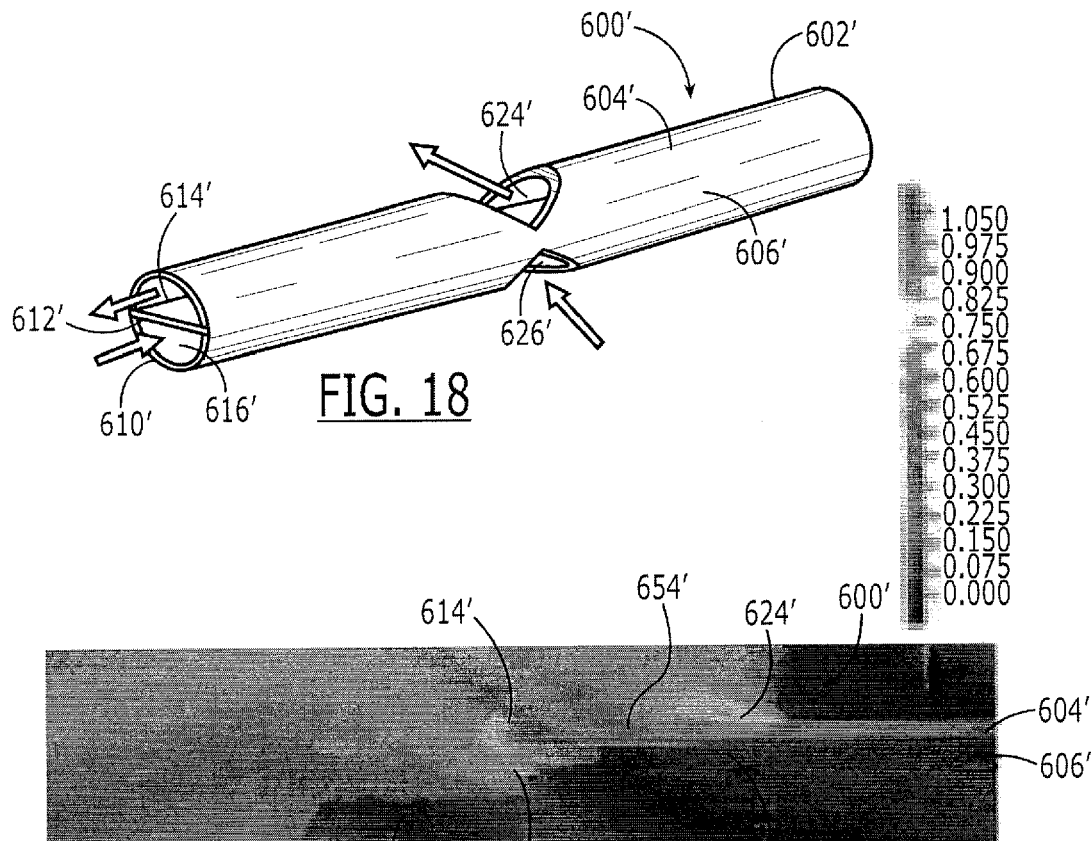
FIG. 18 is a perspective view of a catheter according to an embodiment of the present invention.
Figure 19:
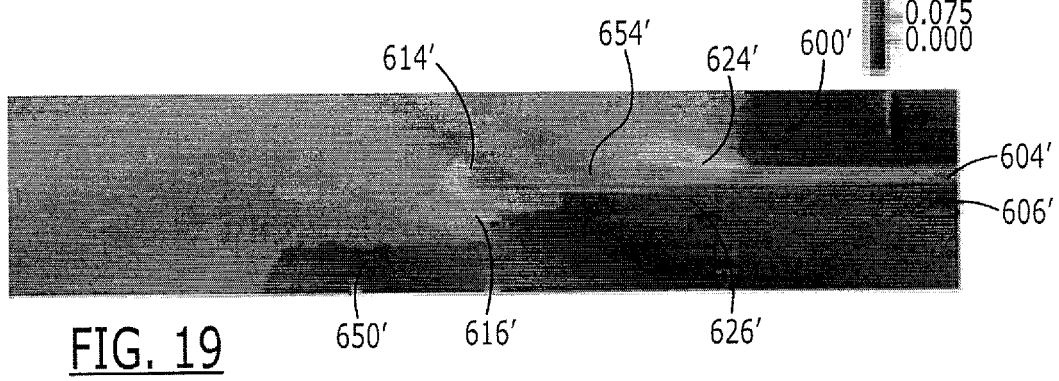
FIG. 19 is a side view of the catheter of FIG. 18 showing a computed flow pattern around a distal tip thereof.

As shown in FIGS. 18 and 19, the orifices 614', 616' of a tip 600' oriented at angles of approximately 80° relative to the partition 612' to shorten the tip 600'. A computational fluid dynamics analysis of the flow generated by the tip 600' described above in the reverse mode of operation is shown in FIG. 19. The tip 600' operates in a manner substantially similar to that of the tip 600, with filtered blood 654' flowing simultaneously out of the orifices 614', 624' and unfiltered blood 650' returning via the orifice 616'. In the exemplary embodiment, the numerical modeling predicts a recirculation rate of about 3% for the conditions shown in FIG. 19. It is believed that, although the performance of the tip 600 was measured as substantially the same as that of the tip 600', the differences in geometry may result in different performance in vivo.

The present invention has been described with reference to specific embodiments, and more specifically to a dialysis catheter with multiple lumens. However, other embodiments may be devised that are applicable to different catheters (e.g., PICC, tunneled central, angiography, ERCP and drainage catheters) without departing from the scope of the invention. Accordingly, various modifications and changes may be made to the embodiments, without departing from the broadest spirit and scope of the present invention as set forth in the claims that follow. The specification and drawings are accordingly to be regarded in an illustrative rather than restrictive sense.

What is claimed is:

1. A flow control tip for a catheter, comprising:
   a partition dividing the catheter into first and second lumens;
   a first orifice fluidly connected to the first lumen and a second orifice fluidly connected to the second lumen, the first orifice being proximal to the second orifice;
   an elongate protrusion extending along a portion of the partition substantially along a centerline of the elongated body, wherein the protrusion protrudes substantially equally into the first and the second lumens, and wherein the protrusion comprises a diverting structure formed by a surface of the protrusion to direct flow from the first orifice away from the centerline.

2. The flow control tip according to claim 1, further comprising a substantially cylindrical outer shell defining an outer wall of the first and the second lumens.

3. The flow control tip according to claim 1, wherein the diverting structure is located approximately halfway between the first and the second orifices.

4. The flow control tip according to claim 1, wherein the protrusion is substantially hemispherical in cross-section, a radius of the protrusion being smaller than a radius of the elongated body.

5. The flow control tip according to claim 1, wherein the diverting structure includes a first portion extending from an outermost extent of the protrusion toward the partition in a proximal to distal direction and a second portion extending away from the partition toward the outermost extent of the protrusion.

6. The flow control tip according to claim 1, wherein the protrusion further comprises a third lumen that includes a radial opening located between the first and the second orifices.

7. The flow control tip according to claim 1, wherein the diverting structure is skived into the protrusion.

8. The flow control tip according to claim 1, wherein the diverting structure is cut into the protrusion.

9. The flow control tip according to claim 1, wherein the protrusion is a solid body.

10. The flow control tip according to claim 1, wherein the diverting structure includes a downward sloping portion and an upward sloping portion.

11. A tip for a catheter, comprising:
an outer wall defining first and second lumens separated from one another by a partition;
a first opening at a distal end of the tip on a first side of the partition opening the first lumen to an exterior of the tip, the outer wall at the first opening defining a first acute angle with the partition so that a proximal end of the first opening is located proximally of the distal end of the tip;
a second opening at the distal end of the tip on a second side of the partition opening the second lumen to the exterior of the tip, the outer wall at the second opening defining a second acute angle with the partition so that a proximal end of the second opening is located proximally of the distal end of the tip; and
a third opening located proximally of the first opening on the first side of the partition opening the first lumen to an exterior of the tip.

12. The catheter tip according to claim 11, wherein the first opening is formed in a plane extending at the first acute angle relative to the partition.

13. The catheter tip according to claim 11, wherein the first opening is formed along a curve intersecting the partition at the first acute angle.

14. The catheter tip according to claim 11, wherein the first acute angle is between 10° and 85°.

15. The catheter tip according to claim 11, further comprising a fourth opening located proximally of the second opening on the second side of the partition opening the second lumen to an exterior of the tip.

16. The catheter tip according to claim 11, wherein a periphery of a proximal portion of the third opening extends substantially in a plane extending distally from a proximal end of the third opening toward the partition at a third acute angle.

17. The catheter tip according to claim 16, wherein a periphery of a distal portion of the third opening extends substantially in a plane extending proximally from a distal end of the third opening toward the partition at a fourth acute angle.

18. The catheter tip according to claim 17, wherein the proximal and distal portions of the third opening meet at points on opposite sides of a longitudinal axis of the tip separated from the partition by a predetermined distance.

19. The catheter tip according to claim 17, wherein the third acute angle is between 10° and 85° and the fourth acute angle is between 10° and 85°.

20. The catheter tip according to claim 17, wherein the third and fourth acute angles are substantially equal to one another.

21. The catheter tip according to claim 15, wherein a periphery of a proximal portion of the fourth opening extends substantially in a plane extending distally from a proximal end of the fourth opening toward the partition at a fifth acute angle.

22. The catheter tip according to claim 21, wherein a periphery of a distal portion of the fourth opening extends substantially in a plane extending proximally from a distal end of the fourth opening toward the partition at a sixth acute angle.

23. The catheter tip according to claim 22, wherein the proximal and distal portions of the fourth opening meet at points on opposite sides of a longitudinal axis of the tip separated from the partition by a predetermined distance.

* * * * *